(12) United States Patent
Mulhauser et al.

(10) Patent No.: US 6,689,111 B2
(45) Date of Patent: Feb. 10, 2004

(54) CONTROLLED EVACUATION OSTOMY DEVICE WITH INTERNAL SEAL

(75) Inventors: Paul Mulhauser, NY, NY (US); Jesse Gala, Summit, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/104,120

(22) Filed: Mar. 22, 2002

(65) Prior Publication Data

US 2003/0181879 A1 Sep. 25, 2003

(51) Int. Cl.[7] ................................................ A61F 5/34
(52) U.S. Cl. ......................................................... 604/332
(58) Field of Search ................................ 604/332–345; 600/32, 30; 128/887

(56) References Cited

U.S. PATENT DOCUMENTS

| 4,344,434 A | 8/1982 | Robertson |
| 4,381,765 A | 5/1983 | Burton |
| 4,662,890 A | 5/1987 | Burton |
| 4,721,508 A | 1/1988 | Burton |
| 4,950,223 A | * 8/1990 | Silvanov .................... 600/32 |
| 5,261,898 A | 11/1993 | Polin et al. |
| 5,569,216 A | 10/1996 | Kim |
| 6,033,390 A | 3/2000 | von Dyck |
| 6,350,255 B1 | 2/2002 | von Dyck |
| 6,485,476 B1 | 11/2002 | von Dyck et al. |

* cited by examiner

Primary Examiner—Weilun Lo
Assistant Examiner—Michael Bogart
(74) Attorney, Agent, or Firm—Stuart E. Krieger

(57) ABSTRACT

A balloon-like member is received in the bowel and inflated to seal the stoma. The member includes a thin, flexible wall defining an opening. A rigid or semi-rigid cap retains the member and closes the opening in the member wall. Skin comfortable adhesive adheres the edge of the cap to the tissue surrounding the stoma. A flexible dilation tube facilitates insertion of the member and cooperates with a pump to inflate the member. The cap is preferably removeably attached to a standard two-piece ostomy faceplate and is provided with a filter element to vent flatus.

114 Claims, 10 Drawing Sheets

CONTROLLED EVACUATION OSTOMY DEVICE WITH INTERNAL SEAL

The present invention relates to ostomy devices of the type adapted to be adhesively affixed to the skin surrounding the stoma and more particularly to such a device which provides a means of controlling evacuation by internally sealing the stoma with a minimum amount of sealing pressure.

Certain surgical procedures known as colostomy, ileostomy and urostomy result in an opening in the abdominal wall, called a stoma, which permits waste discharge from the interior of a body cavity. Since the patient has no control over the waste discharge, it is often necessary for the patients who have undergone these surgical procedures to utilize an ostomy device to protect the stoma and collect the waste material as it is discharged.

Over the years, ostomy devices of a variety of different types and constructions have been utilized. Various materials and adhesives have been developed to increase the utility and wareability of the devices.

The basic device includes a collection receptacle or pouch connected to an adhesive coated faceplate which serves to mount the pouch to the body. The pouch includes first and, second thin film walls which are sealed by heat welding or the like along the periphery. The pouch has an inlet opening designed to be aligned with the stoma and may have an outlet for emptying material from the pouch. In single piece devices, the pouch is permanently affixed to the adhesive coated faceplate. In two-piece devices, the pouch is detachably mounted to the faceplate by coupling rings or the like, permitting the pouch to be replaced without removal of the faceplate each time.

The two-piece device requires a means for releasably mounting the pouch to the faceplate. One particularly successful structure takes the form of a pair of annular or ring-like rigid or semi-rigid plastic parts, one in the form of an axially extending rib and the other in the form of a channel into which the rib may be removably received and frictionally engaged.

These ostomy devices collect waste as it is discharged from the bowel but include no means for controlling when discharge takes place. One of the main objectives of ostomy appliances is to increase the freedom of mobility of the user and the ability of the user to lead a more normal life by participating in various activities. However, having discharge take place into the collection pouch in certain situations may cause embarrassment to the user because of the noise or smell or because of the increase in the size of the pouch. Accordingly, it is desirable to control when evacuation takes place so that it will not occur at times which may cause embarrassment.

It is possible to temporarily seal the stoma to prevent discharge at certain times. However, sealing the stoma normally requires the application of significant local pressure on the mucosal tissue, a result which must be avoided because high local pressure can abrade or otherwise damage the bowel tissue or can prevent blood flow to the tissue if the applied pressure exceeds local capillary pressure.

While it is desirable to prevent the flow of solid or semi-solid stool from the stoma, the same is not true with respect to flatus. As much as two-thirds of the volume of the bowel may be comprised of flatus. This gas must be released for user comfort and to maximize the time between evacuations.

It is also desirable that the sealing device be adapted to couple with a standard two-piece ostomy faceplate and thus be interchangeable with a standard two-piece ostomy pouch. Otherwise, the faceplate will have to be removed each time a new sealing device is mounted, a result which is to be avoided because repeated removal of the device can damage sensitive tissue and cause discomfort.

Those objectives are met in accordance with our invention through the use of a sealing device in the form of a balloon-like sealing member which is received within the bowel to seal the stoma against the discharge of solid or semi-solid stool.

The balloon-like sealing member exerts a low pressure (preferably a range between 10 mm Hg and 30 mm Hg) across a large area of the inner wall of the bowel proximal to the entry of the bowel through the abdominal wall. The sealing member is formed of a thin and flexible wall that is closed at one end and open at the other end. When the sealing member is pressurized, it expands like a balloon, forming a seal with a large contact area with the inner bowel wall. The flexibility of the member wall allows it to conform to the bowel wall. Based on preliminary laboratory test results, the device can prevent release of stool from the bowel with internal bowel pressures up of 50 mm Hg and above.

The sealing member wall is preferably made of a material that is also a good odor barrier. One such wall material would be polyurethane, although silicone rubber, thermoplastic elastomer or one of the wide variety of known multilayer barrier films would also be potentially good candidate materials.

The sealing member could have a variety of configurations to maximize seal effectiveness. One preferred shape would have a relatively large and bulbous proximal end to ensure full contact with the bowel wall in the region proximal to the abdominal wall. The overall diameter and length of the sealing member are also important, and would be selected to maximize effectiveness for users of a variety of body types and stoma shapes.

The sealing member reacts to temporary increases in internal bowel pressure by contracting slightly, thereby equalizing its internal pressure to the pressure in the bowel. The flexible and non-rigid nature of the member gives it complete freedom to move and conform to local changes in bowel pressure and shape.

By design, the seal created by the sealing member would also be slightly "imperfect", such that flatus present at the interface between the exterior member wall and bowel wall would pass along that interface. Solid or semi-solid material, such as stool, would not be allowed to pass.

It is, therefore, a prime object of the present invention to provide a controlled evacuation ostomy device which includes an internal seal.

It is another object of the present invention to provide a controlled evacuation ostomy device with an internal seal in the form of an inflatable balloon-like sealing member that seals the stoma effectively while exerting only a minimum amount of sealing pressure.

It is another object of the present invention to provide a controlled evacuation ostomy device with an internal seal which prevents the discharge of solid and semi-solid stool but permits the release of flatus.

It is another object of the present invention to provide a controlled evacuation ostomy device with an internal seal which is deployed by insertion of the sealing member into the stoma, proximate to the abdominal wall.

It is another object of the present invention to provide a controlled evacuation ostomy device with an internal seal in which the sealing member is inserted into the bowel in the deflated condition and is thereafter inflated to conform to the shape of the inner wall of the bowel that surrounds it.

It is another object of the present invention to provide a controlled evacuation ostomy device with an internal seal in which the internal sealing pressure of the sealing member increases when exposed to an increase in internal bowel pressure.

It is another object of the present invention to provide a controlled evacuation ostomy device with an internal seal which is compatible with a standard two-piece ostomy device.

In accordance with one aspect of the present invention, an ostomy device is provided including a balloon-like member adapted to be received in the bowel and inflated to seal the stoma. The sealing member includes a flexible wall defining an opening. Cap means for retaining the member wall and closing the opening in the member are provided, as are means for adhering the cap means to the tissue proximate the stoma.

The sealing member preferably has a bulbous proximal end. The bulbous proximal end permits the wall of the member to fully contact the bowel.

The cap means has an inflation port. Means are provided for inflating the member through this port. Flexible tube means extend from the cap means and into the member. The flexible tube means defines an inflation channel connected to the inflation port. A one-way valve is associated with the inflation port.

The inflation means includes pump means with a nozzle. The nozzle is adapted to be received in the inflation port in the cap means. Relief valve means are associated with the pump means to prevent overinflation of the sealing member.

The means for adhering the cap to the tissue includes a faceplate. Means are provided for detachably mounting the cap means on the faceplate.

The faceplate includes a first engaging part. The detachable mounting means includes a second engaging part. The second engaging part defines an opening. The parts are adapted to inter-engage with the opening of the second engaging part aligned with the stoma.

The detachable mounting means also includes a member wall retaining part in the form of a disc with an opening. A waste collection receptacle is provided. The receptacle has a first inlet aligned with the second engaging part opening and a wall defining a second inlet. The portion of the receptacle wall proximate the second inlet is sealed to the retaining disc.

A channel is defined between the wall of the sealing member and the interior wall of the receptacle. Filter means are operably interposed between the channel and the environment. The filter means are preferably situated in the retaining disc.

Means are provided for detachably mounting the cap means on the second engaging part. The retaining disc is adapted to be received between the cap means and the second engaging part.

In accordance with another aspect of the present invention, an ostomy device is provided with a balloon-like member adapted to be received in the bowel and inflated to seal the stoma. The device includes a faceplate and means for adhering the faceplate to the tissue surrounding the stoma. The sealing member includes a flexible wall defining an opening. Cap means are provided for retaining the member wall and closing the opening in the member. The cap means includes an inflation port. Means are also provided for mounting the cap means on the faceplate.

Inflating means, in the form of a hand pump with a nozzle, are provided. The nozzle is adapted to be removably connected to the inflation port. The inflating means can alternatively be incorporated as integral feature in the cap.

A waste collection receptacle is operably interposed between the cap means and the faceplate. The cap means mounting means includes means for detachably engaging the faceplate and means for detachably mounting the cap means on the faceplate engaging means. The faceplate engaging means also includes a member retaining disc. The receptacle wall is affixed to the retaining disc. The retaining disc includes filter means through which flatus is vented to the environment.

The faceplate includes a first engaging part. The faceplate engaging means includes a second engaging part. These parts inter-exchange to detachably mount the cap on the faceplate.

The cap means also includes a flexible tube with an inflation channel. The tube is received in the member. A one-way valve is associated with the inflation channel.

To these and to such other objects which may hereinafter appear, the present invention relates to an controlled evacuation ostomy device with an internal seal, as described in detail in the following specification and recited in the annexed claims, taken together with the accompanying drawings, wherein like numerals refer to like parts and in which:

Figure 1:
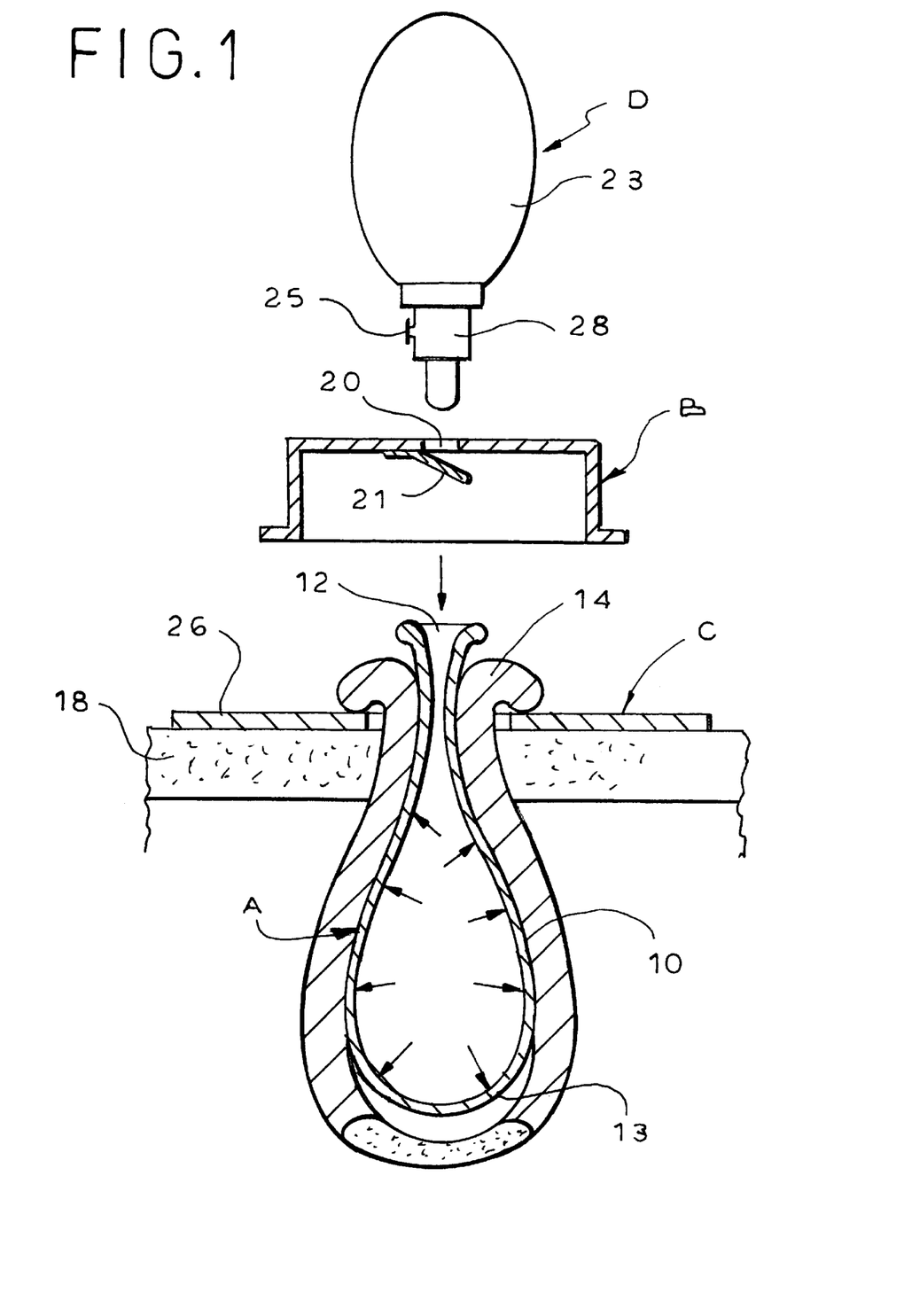
FIG. 1 is an exploded schematic view illustrating the concept of the present invention.

FIG. 1 illustrates the concept of the present invention. As illustrated in that figure, the ostomy device of the present invention includes a balloon-like sealing member, generally designated A, which is formed of a thin, flexible wall 10 with an opening 12 and a bulbous proximate end 13. Member A is adapted to be inserted into the bowel through stoma 14.

The portion of wall 10 of member A proximate opening 12 is fixed to the interior surface of the top wall of a cap, generally designated B. Cap B retains the sealing member with the opening 12 external to stoma 14 and serves to close the opening in the member. Cap B is made of rigid or semi-rigid material. Adhesive means, generally designated C, is provided for adhering the bottom edge of cap B to the tissue 18 surrounding the stoma.

Cap B is provided with an inflation port 20. A one-way or "check" valve 21 is associated with port 20. Valve 21 may simply be a flexible flap, one end of which is fixed to the underside of the top wall of cap B, proximate port 20.

Inflation means, generally designated D, are provided in the form of a hand pump with a flexible bulb 23 and a nozzle with a rigid part 28. A relief valve 25 of conventional design is associated with nozzle part 28 to prevent overinflation of member A. Alternatively, a smaller pump could be incorporated as an integral part of the cap.

The nozzle is inserted into inflation port 20 in cap B and bulb 23 is squeezed to inflate member A. Once inflated, member A seals the stoma. The nozzle is then withdrawn. As the nozzle is withdrawn, valve 21 closes port 20 to maintain the pressure in member A.

Member A is preferably made of material that is thin, flexible and has good barrier properties. One such material would be polyurethane, although silicone rubber, theremoplastic elastomers, or a multiplayer barrier film would also be potentially good candidate materials.

Member A could have a variety of configurations to maximize seal effectiveness. One preferred shape, illustrated in the drawings, has a relatively large tube-like configuration with a bulbous proximal end to ensure full contact with the bowel wall in the region proximal to the abdominal wall. The overall diameter and length of the sealing member are also important. They could be key factors in maximizing effectiveness for users of a variety of body types and stoma shapes.

Because of the flexible and compliant nature of member A, it reacts to temporary increases in internal bowel pressure by contracting slightly, thereby equalizing its internal pressure to the pressure in the bowel. The flexible and non-rigid characteristics of the sealing member give it complete freedom to move and conform to local changes in bowel pressure and shape.

By design, the seal created by member A is slightly "imperfect", in that flatus that is present at the interface between the member wall and bowel wall would be allowed to pass along that interface. Solid or semi-solid material, such as stool, would not be allowed to pass.

Member A could be attached directly to the underside of the top wall of cap B. Cap B is preferably temporarily attached to the skin around the stoma by a flexible membrane with a layer of skin compatible adhesive, commonly called a faceplate 26. However, as indicated below, it is preferable to incorporate a means for detachably mounting cap B to the faceplate to avoid repeated removals of the adhesive member.

Figure 2:
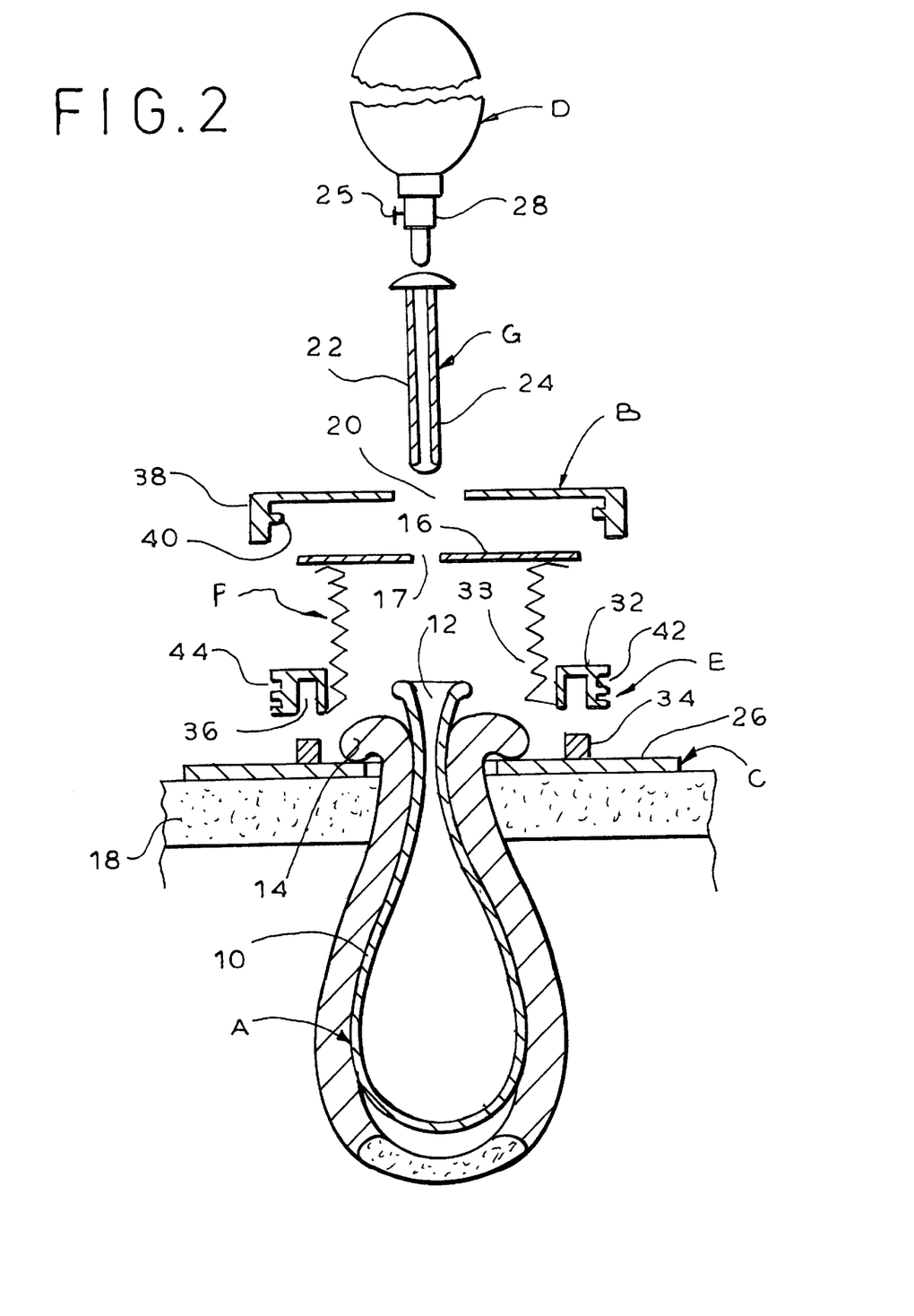
FIG. 2 is an exploded schematic view showing the components of the preferred embodiment of the present invention.
Figure 3:
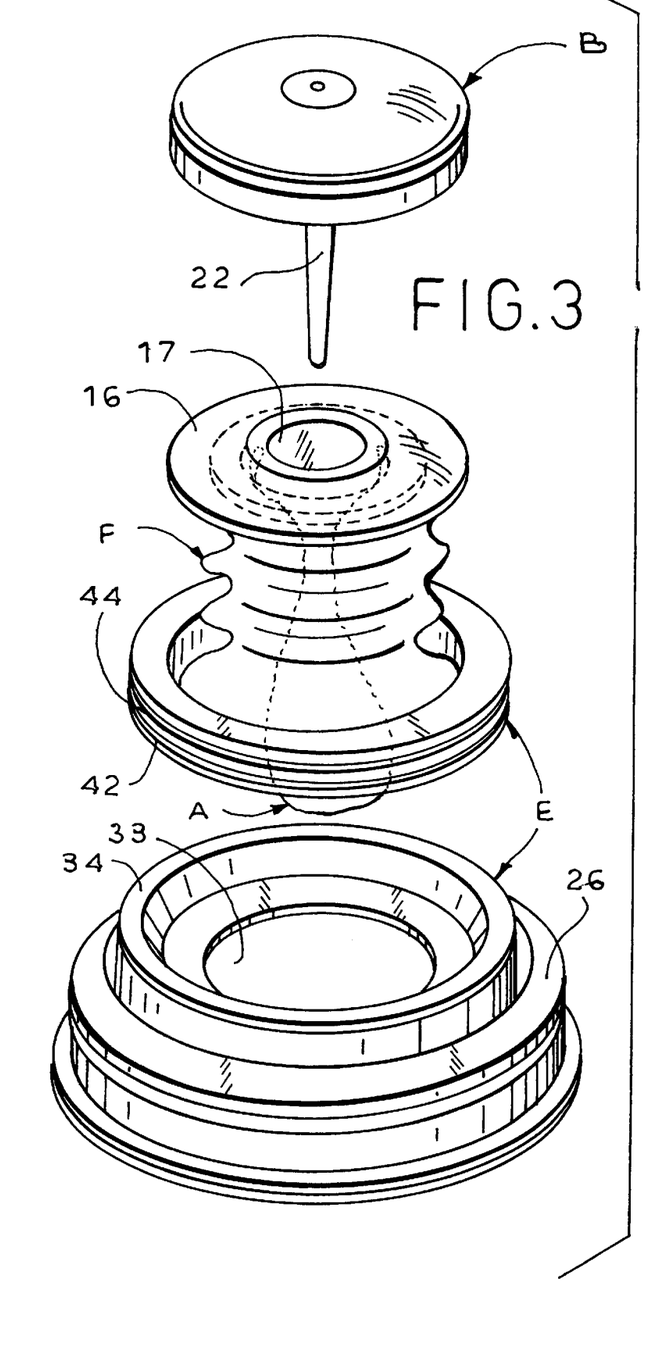
FIG. 3 is an exploded isometric view of the components of the preferred embodiment of the present invention.
Figure 4:
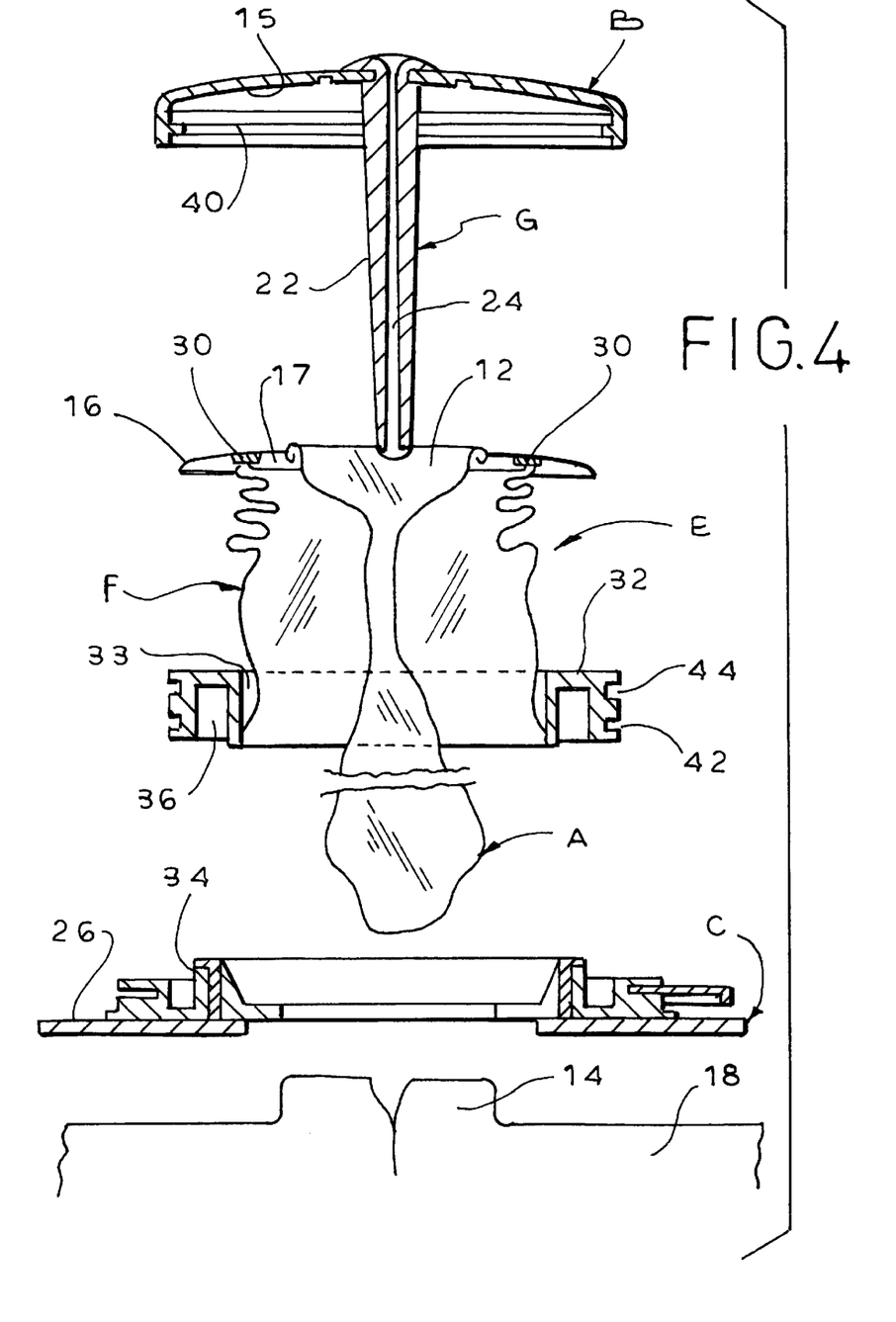
FIG. 4 is an exploded cross-sectional view of the device shown in FIG. 3.

FIGS. 2, 3 and 4 illustrate the preferred embodiment of the ostomy device. The preferred embodiment includes the balloon-like sealing member A, cap B, adhesive means adhering means C and inflation means D, as described previously. However, in this embodiment, means, generally designated E, for detachably mounting cap B to faceplate 26, a waste collection receptacle, generally designated F, and dilator means, generally designated G, are present.

Means E includes a retaining disc 16 and a base member 32. It also includes a first engaging part, in the form of an annular protrusion or rib 34, extending from the surface of faceplate 26.

Member 32 is annular in configuration and includes a second engaging part in the form of an annular channel 36. Member 32 defines a central opening 33 which aligns with the stoma.

Rib 34 is received in channel 36 in a detachable manner and forms a fluid-tight seal between faceplate 26 and base member 32. These interengaging parts may have the same configuration as used on conventional two-piece ostomy devices.

The side wall 38 of cap B is provided with an inwardly directed protrusion 40. The exterior wall 42 of base member 32 has a circumferential grove 44 into which protrusion 40 "snap fits" to secure cap B on base member 32. This is one possible embodiment of a means to removably attach cap B to base member 32. It can be envisaged that many other methods of attaching cap to base member could be implemented to produce this product.

Figure 5:
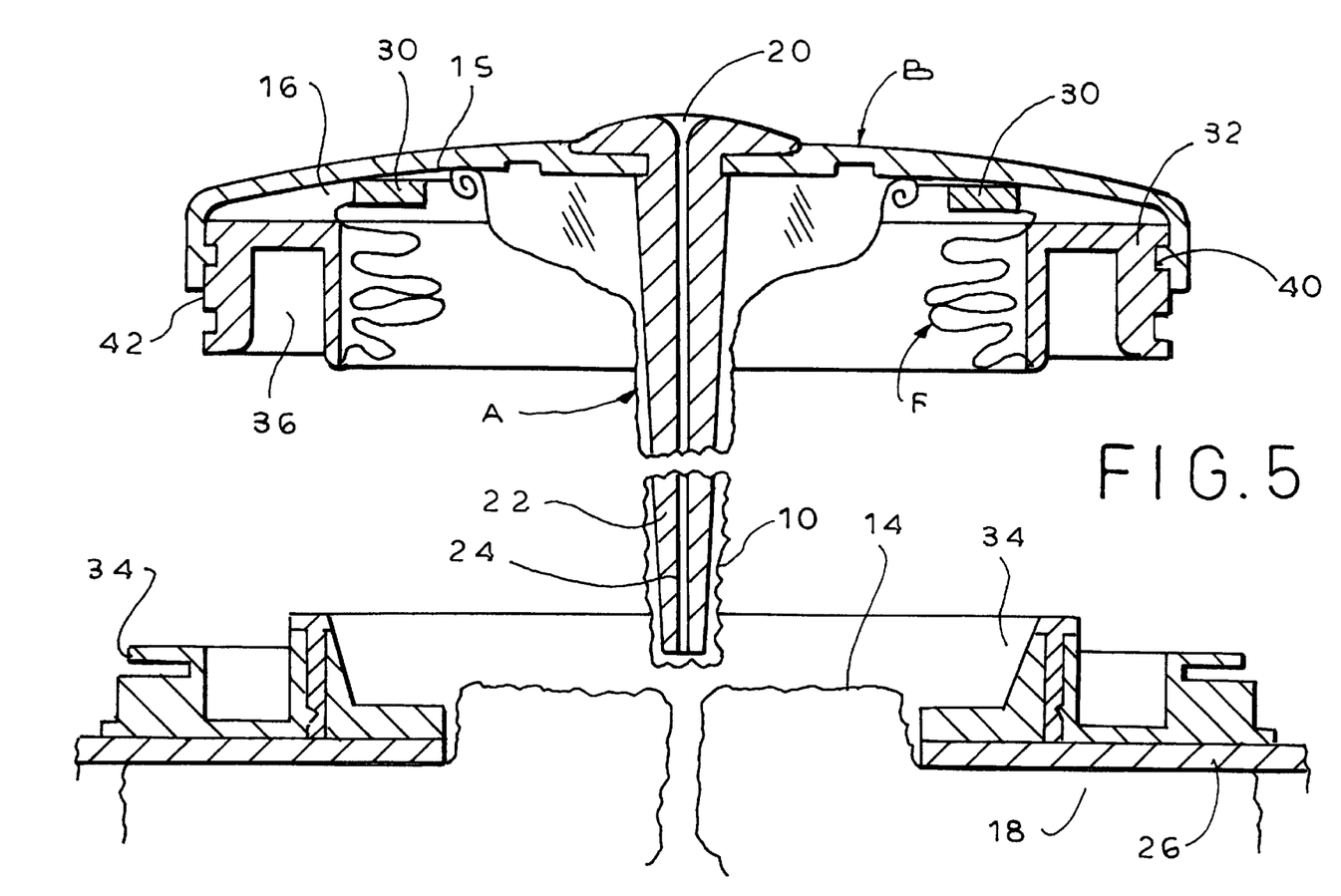
FIG. 5 is a cross-sectional view of the device of FIG. 3, shown prior to mounting of the cap.

As illustrated in FIG. 5, retaining disc 16 is situated between the undersurface of the top wall 15 of cap B and base member 32. Disc 16 has a central opening 17 which aligns with opening 12 in member A. The portion of wall 10 of member A proximate opening 12 is secured to disc 16. When cap B is received on base member 32 wall 10 of member A is retained and opening 12 covered.

Member A, being completely flexible, could be inserted into the stoma by dilator means G, which takes the form of a flexible dilator tube 22. Tube 22 is located inside member A, but is not attached to the wall 10. Dilator tube 22 serves to aid insertion of the member A into the stoma. Once the member A is inserted, dilator tube 22 remains in place but is small and flexible so as not to cause irritation or discomfort to the user. Dilator tube 22 also delivers air for inflation of the member A through internal inflation channel 24.

Figure 6:
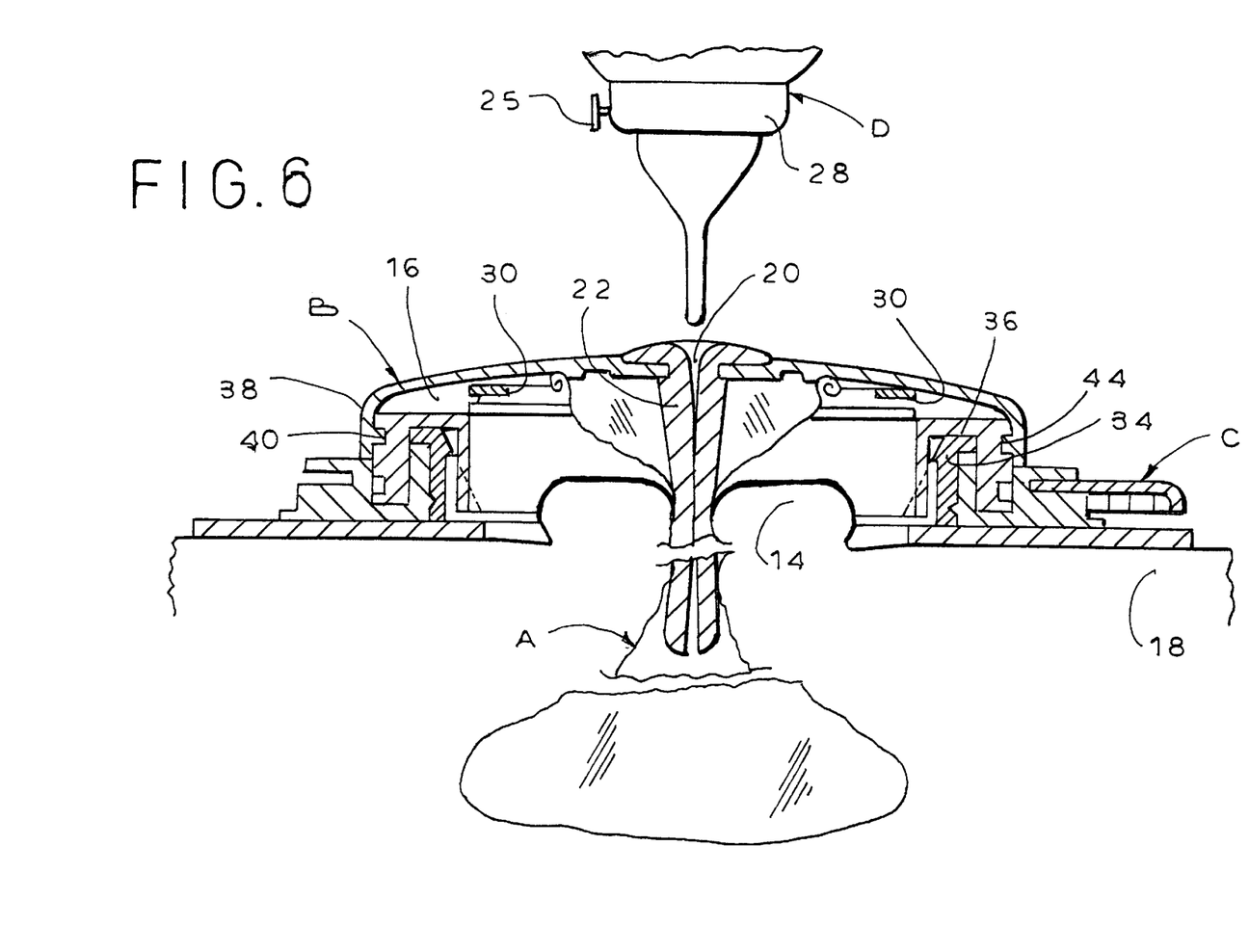
FIG. 6 is a cross-sectional view of the device of FIG. 3, after inflation of the sealing member.

As illustrated in FIG. 6, the seal can be pressurized by inflation means D which could take the form of an external inflator bulb 23. The nozzle is received through port 20 in cap B and into dilator tube 22. Bulb 23 is squeezed to pressurize the seal. Dilator tube 22 incorporates an internal one-way valve (not shown) to prevent air leakage from behind the seal. The pump could also be an integral feature incorporated into the design of the cap.

Limiting the pressure applied to the seal is also a key concern. Our goal is to ensure that sealing pressure exerted on the bowel or stoma does not exceed local capillary pressure, to prevent necrosis of mucosal tissue. For this reason, a pressure relief valve 25 that will open at pressures exceeding a pre-set limit is provided. Preferably, this valve is incorporated into inflation means D, such as in nozzle part 28, and would not have to be built into the device itself. Relief valve 25 prevents overinflation of member A.

The seal created by the member A is, by design, not a perfect seal. Slight irregularities in the bowel wall and/or slight wrinkles that form in the seal material create very small leak paths. In practice, these leak paths are too small for solid or semi-solid stool to pass, but would allow any flatus that is present at the face of the seal to be released.

Once flatus has been released past the seal, it is possible for it to be filtered by means of one or more filtration elements 30 situated in disc 16, as shown in FIGS. 4, 5 and 6. An activated carbon filter, identical to those used in conventional ostomy pouches, may be used for this purpose.

Figure 10:
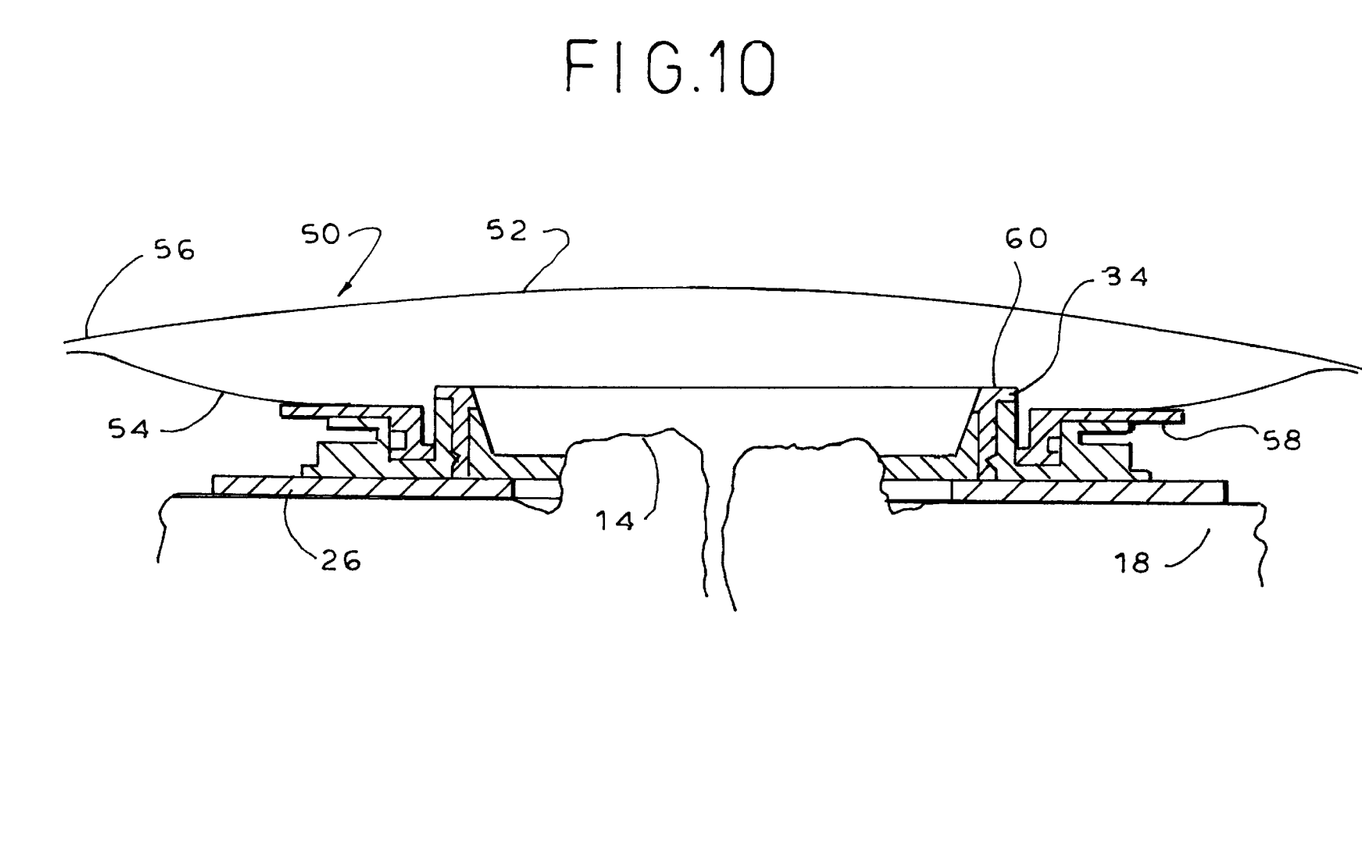
FIG. 10 illustrates the faceplate of the preferred embodiment of the present invention with a standard two-piece ostomy pouch mounted thereto.

The cap B can be attached to the skin 18 surrounding the stoma 14 by a variety of means, including a layer of a temporary skin compatible adhesive similar to the adhesives used to attach a conventional one-piece ostomy pouch to the skin. However, it is preferable to mate cap B to a standard two-piece ostomy faceplate 26, as illustrated. The cap would connect to the faceplate in the same manner as a two-piece ostomy pouch. It would be interchangeable with a two-piece ostomy pouch, as illustrated in FIG. 10, so that the user would have the option at any time to use the controlled evacuation device or a standard ostomy pouch.

As seen in FIG. 6, inwardly extending lip 40 on the interior surface of cap side wall 38 is received within groove 44 in exterior wall 42 of base 32. Cap B fits over base 32, with disc 16 situated therebetween. The cap seals the opening in member A.

Figure 7:
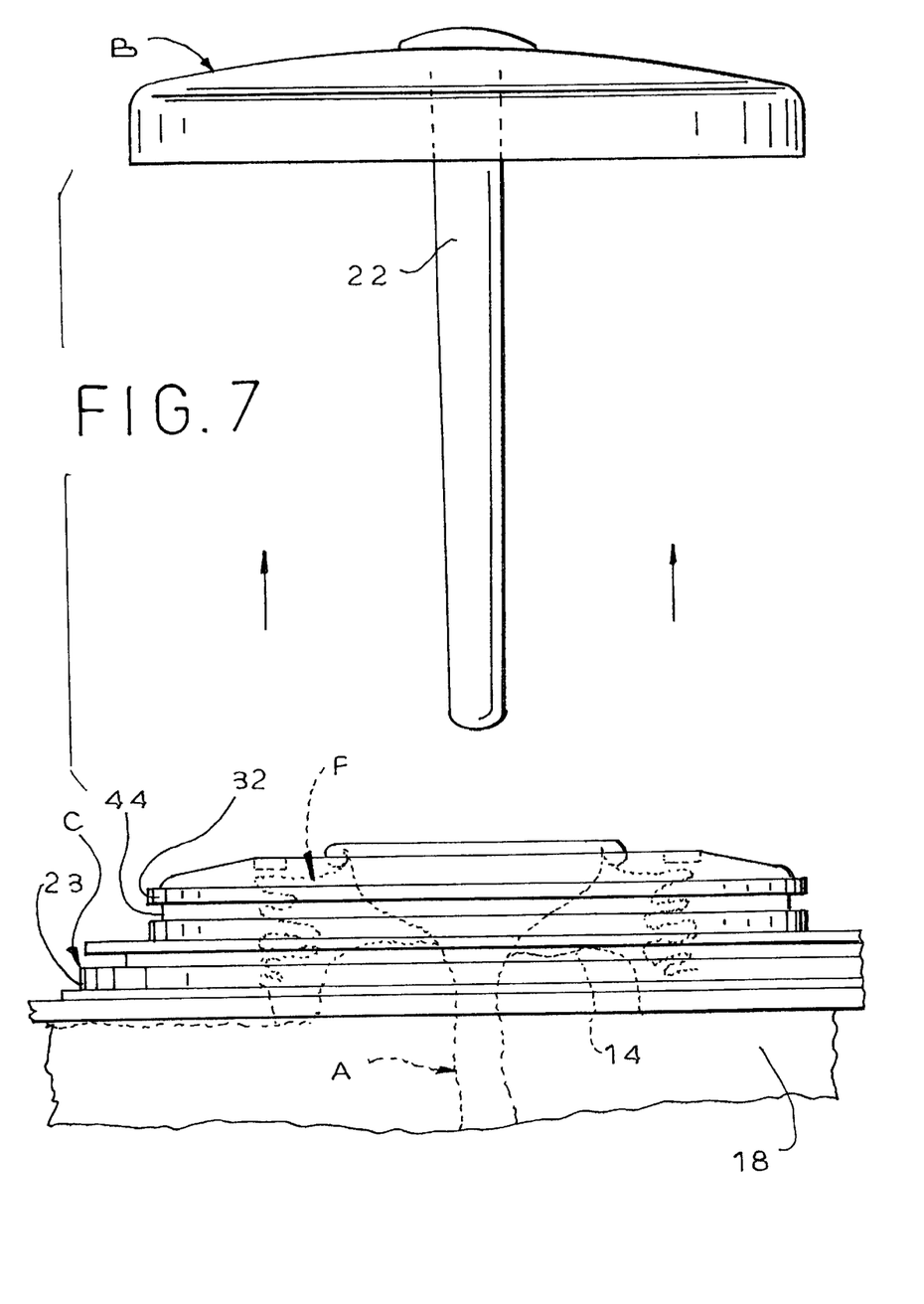
FIG. 7 is a view of the device of FIG. 3, shown after removal of the cap.

When cap B is removed, as seen in FIG. 7, the contents of the bowel will be evacuated and must be disposed of. One means of facilitating disposal is to incorporate a disposal pouch F into the controlled evacuation device Pouch F preferably has a tubular configuration. It is made of thin, flexible plastic film and is concentric with the central axis of the device. Pouch F is mounted between disc 16 and base member 32. It has an opening aligned with opening 33 in member 32. Pouch F is preferably collapsed into a thin annular space for storage in the device, as seen in FIG. 5. It can be envisaged that many other alternative configurations are also appropriate for a self-contained disposal pouch.

Figure 8:
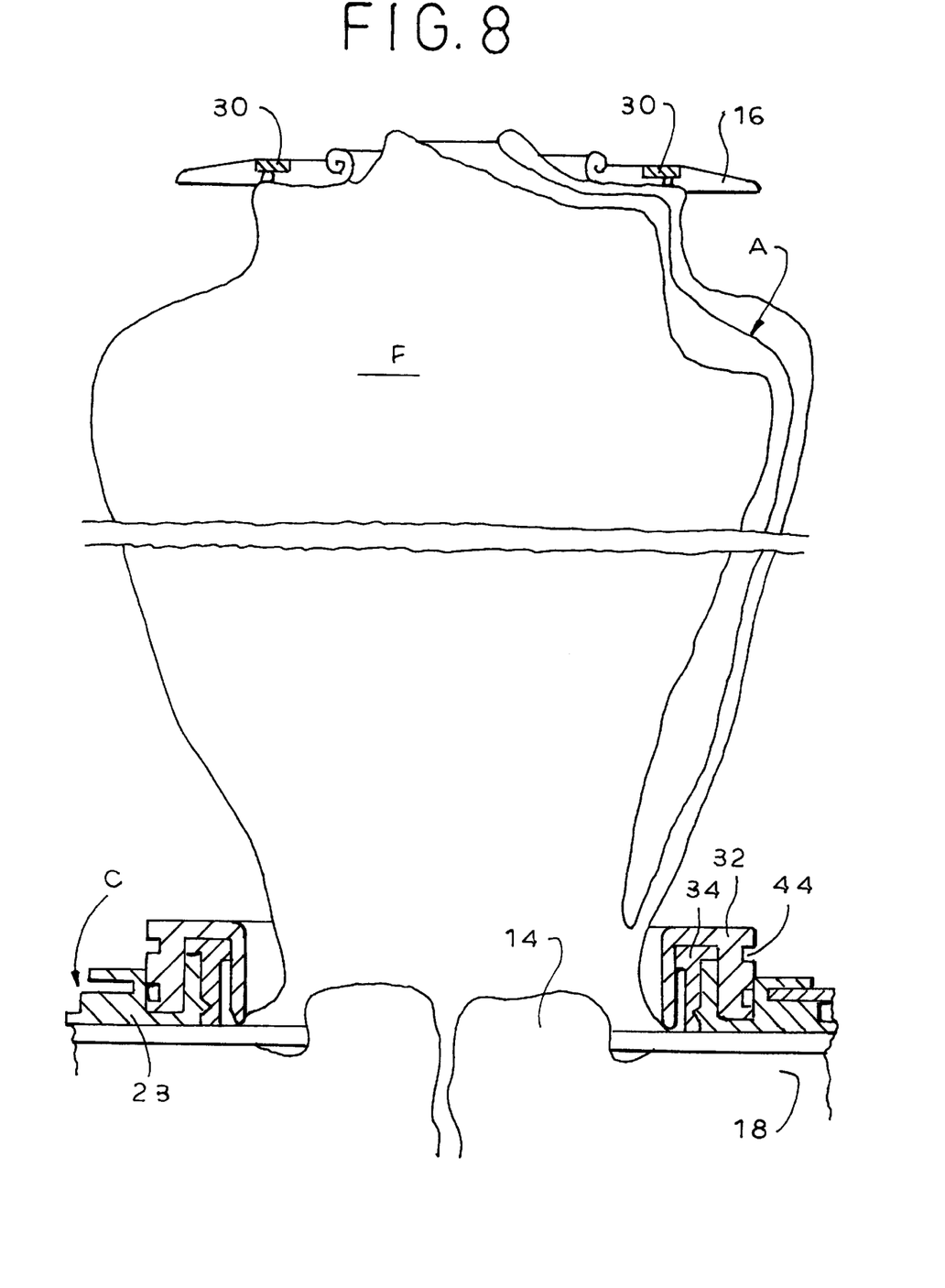
FIG. 8 is a cross-sectional view of the sealing member of the device of FIG. 3, shown after evacuation.
Figure 9:
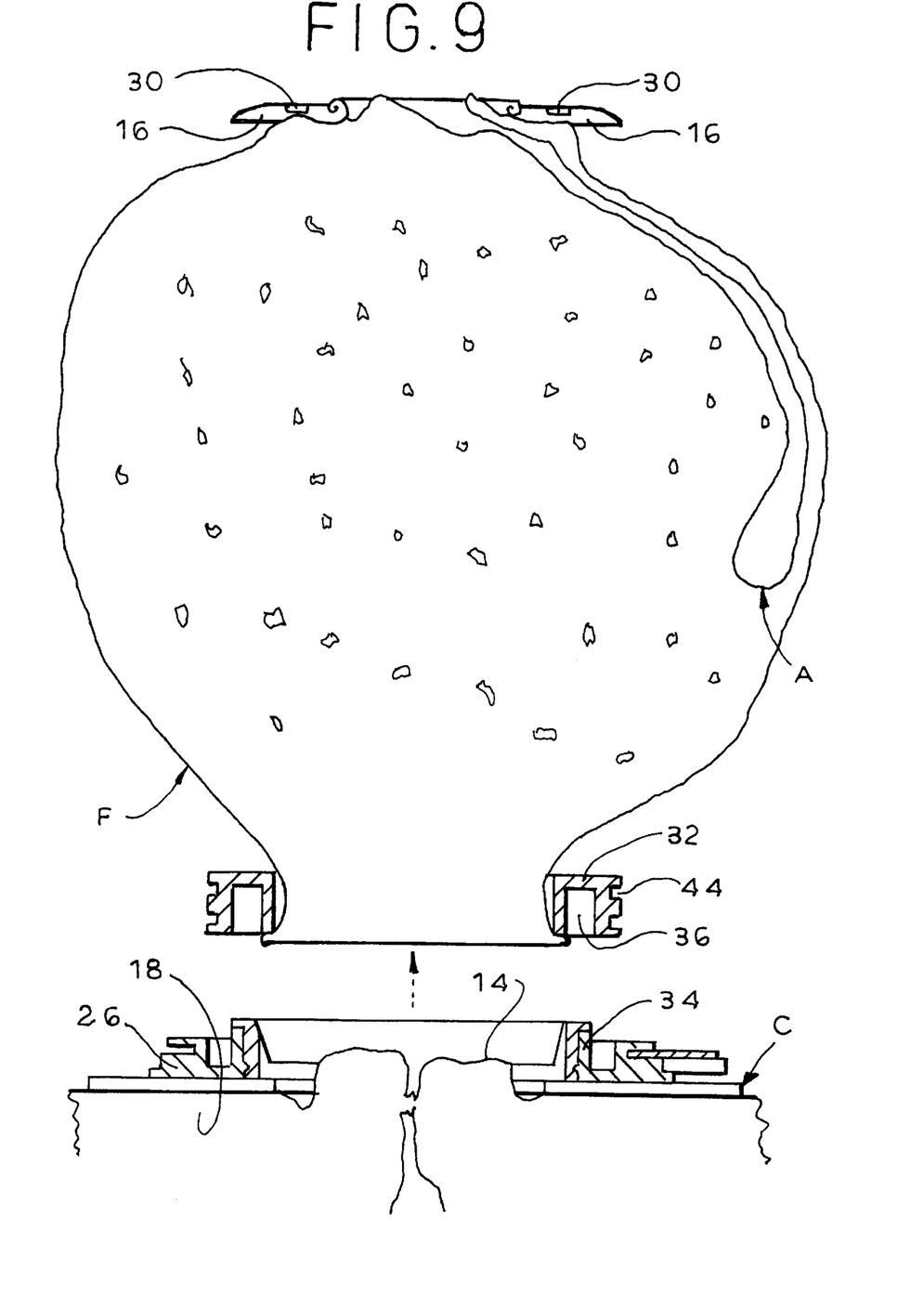
FIG. 9 is a cross-sectional view of the sealing member of FIG. 3, shown after detachment from the faceplate.

When evacuation is required, the user would detach the cap B from base number 32, leaving the base member 32 attached to the faceplate 26, as seen in FIG. 7. One end of pouch F remains attached to disc 16, the other end to base member 32. Removal of the cap releases the seal to permit evacuation into the pouch expanding the pouch, much like the bellows of a concertina. Once the contents of the bowel are released to the pouch, as seen in FIG. 8, base member 32 is removed from the faceplate, as seen in FIG. 9, and the entire disc/pouch/base assembly is disposed of in a suitable refuse container.

FIG. 10 shows a conventional two-piece ostomy pouch 50 which includes walls 52 and 54 sealed around their periphery 56. Pouch 50 includes an annular engaging member 58 with a channel 60 designed to receive rib 34 on faceplate 26 in the same manner as base member 32 is received on the faceplate. Thus, either pouch 50 or the device of the present invention could be received on faceplate 26.

It will now be appreciated that the present invention relates to a controlled evacuation ostomy device which includes a balloon-like member designed to be received in the bowel and inflated to seal the stoma. The device applies a minimum amount of pressure on the tissue and is flexible and compliant, resulting in a comfortable means of controlling when evacuation takes place. An internal dilator tube is provide to facilitate insertion and inflation of the member. A collection receptacle is also provided as part of the device.

While only a limited number of preferred embodiments have been disclosed for purposes of illustration, it is obvious that many variations and modifications could be made thereto. It is intended to cover all of these variations and modifications which fall within the scope of the present invention, as set forth in the following claims:

We claim:

1. An ostomy device for insertion through the stoma into the bowel comprising a balloon-like member adapted to be inserted into the bowel and inflated to seal the stoma, said member comprising a flexible wall defining an opening, cap means for retaining said wall and closing said opening, and means for adhering said cap means to the tissue proximate the stoma, wherein said adhering means comprises a faceplate and means for detachably mounting said cap means on said faceplate and means for inflating said member while said cap means is mounted on said faceplate.

2. The device of claim 1 wherein said cap means comprises a port, flexible tube means connected to said port, said tube means being adapted to extend into said member and comprising an inflation channel.

3. The device of claim 2 wherein said inflating means further comprises pump means adapted to be connected to said inflation channel through said port.

4. The device of claim 3 wherein said tube means comprises a one-way valve.

5. The device of claim 2 wherein said inflating means comprises a hand pump comprising a nozzle adapted to be removably connected to said tube means, in communication with said inflation channel.

6. The device of claim 1 wherein said inflating means comprises a pressure relief valve.

7. The device of claim 1 wherein said faceplate comprises a first engaging part defining an opening, and said cap means mounting means comprises a second engaging part with an opening, said parts being adapted to engage, with said opening in said second engaging part aligned with the stoma.

8. The device of claim 7 wherein said detachable mounting means further comprises a member retaining part defining an opening and a waste collection receptacle having a first inlet aligned with said second engaging part opening and a wall defining a second inlet, said receptacle wall being sealed to said member retaining part with said second inlet aligned with said opening in said member retaining part.

9. The device of claim 8 further comprising a channel defined between said wall of said member and the interior wall of said receptacle and filter means operably interposed between said channel and the environment.

10. The device of claim 9 wherein said filter means is situated in said retaining part.

11. The device of claim 7 further comprising means for detachably mounting said cap means on said second engaging part.

12. The device of claim 7 wherein said member retaining part comprises a disc and wherein said disc is adapted to be received between said cap means and said second engaging part.

13. The device of claim 1 wherein said member comprises a bulbous proximal end.

14. An ostomy device for insertion through the stoma into the bowel comprising a balloon-like member adapted to be inserted into the bowel and inflated to seal the stoma, said member comprising a flexible wall defining an opening, cap means for retaining said wall and closing said opening and means for adhering said cap means to the tissue proximate the stoma, means for inflating said member, wherein said cap means comprises a port, flexible tube means connected to said port, said tube means being adapted to extend into said member and comprising an inflation channel, wherein said inflating means comprises a hand pump comprising a nozzle adapted to be removably connected to said tube means, in communication with said inflation channel.

15. The device of claim 14 wherein said adhering means comprises a faceplate and means for detachably mounting said cap means on said faceplate.

16. An ostomy device for insertion through the stoma into the bowel comprising a balloon-like member adapted to be received in the bowel and inflated to seal the stoma, a faceplate, means for adhering said faceplate to the tissue surrounding the stoma, said member comprising a flexible wall defining an opening, cap means for retaining said wall and closing said opening in said member, said cap means comprising an inflation port and means for mounting said cap means on said faceplate, and a waste collection receptacle operably interposed between said cap means and said faceplate, wherein said cap means mounting means comprises means for detachably engaging said faceplate and means for detachably mounting said cap means on said faceplate engaging means and means for inflating said member while said cap means is mounted on said faceplate.

17. The device of claim 16 further comprising means for inflating said member.

18. The device of claim 16 further comprising a channel defined between said wall of said member and the interior wall of said receptacle, and filter means operably interposed between said channel and the environment.

19. The device of claim 16 wherein said member comprises a bulbous proximal end.

20. An ostomy device for insertion through the stoma into the bowel comprising a balloon-like member adapted to be received in the bowel and inflated to seal the stoma, a faceplate, means for adhering said faceplate to the tissue surrounding the stoma, said member comprising a flexible wall defining an opening, cap means for retaining said wall and closing said opening in said member, said cap means comprising an inflation port, and means for mounting said cap means on said faceplate, wherein said faceplate comprises a first engaging part and said cap means mounting means comprises a second engaging parts, and means for inflating said member while said cap means is mounted on said faceplate.

21. An ostomy device for insertion through the stoma into the bowel comprising a balloon-like member adapted to be received in the bowel and inflated to seal the stoma, a faceplate, means for adhering said faceplate to the tissue surrounding the stoma, said member comprising a flexible wall defining an opening, cap means for retaining said wall and closing said opening in said member, said cap means comprising an inflation port, and means for mounting said cap means on said faceplate, a waste collection receptacle operably interposed between said cap means and said faceplate, a channel defined between said wall of said member and the interior wall of said receptacle, and filter means operably interposed between said channel and the environment, wherein said cap means mounting means comprises a member retaining part to which said member wall is affixed, and means for inflating said member while said cap means is mounted on said faceplate.

22. The device of claim 20 wherein said filter means is situated in said retaining part.

23. An ostomy device for insertion through the stoma into the bowel comprising a balloon-like member adapted to be received in the bowel and inflated to seal the stoma, a faceplate, means for adhering said faceplate to the tissue surrounding the stoma, said member comprising a flexible wall defining an opening, cap means for retaining said wall and closing said opening in said member, said cap means comprising an inflation port, means for mounting said cap means on said faceplate, and means for inflating said member, wherein said inflating means comprises a hand pump comprising a nozzle adapted to be removably connected to said inflation port.

24. An ostomy device for insertion through the stoma into the bowel comprising a balloon-like member adapted to be inserted into the bowel and inflated to seal the stoma, said member comprising a flexible wall defining an opening, cap means for retaining said wall and closing said opening and means for adhering said cap means to the tissue proximate the stoma, wherein said member comprises a bulbous proximal end so as to provide a large surface contact area between said member and the bowel wall when inflated.

25. The device of claim 24 further comprising means for inflating said member.

26. The device of claim 25 wherein said cap means comprises a port, flexible tube means connected to said port, said tube means adapted to extend into said member and comprising an inflation channel.

27. The device of claim 26 wherein said inflating means further comprises pump means adapted to be connected to said inflation channel through said port.

28. The device of claim 26 wherein said inflating means comprises a hand pump comprising a nozzle adapted to be removably connected to said tube means, in communication with said inflation channel.

29. The device of claim 25 wherein said inflating means comprises a pressure relief valve.

30. The device of claim 26 wherein said tube means comprises a one-way valve.

31. The device of claim 24 wherein said adhering means comprises a faceplate and means for detachably mounting said cap means on said faceplate.

32. The device of claim 31 wherein said faceplate comprises a first engaging part defining an opening, and said cap means mounting means comprises a second engaging part with an opening, said parts being adapted to engage with said opening in said second engaging part aligned with the stoma.

33. The device of claim 32 wherein said cap means mounting means further comprises a member retaining part defining an opening and a waste collection receptacle having a first inlet aligned with said second engaging part opening and a wall defining a second inlet, said receptacle wall being sealed to said member retaining part with said second inlet aligned with said opening in said member retaining part.

34. The device of claim 33 further comprising a channel defined between said wall of said member and the interior wall of said receptacle and filter means operably interposed between said channel and the environment.

35. The device of claim 34 wherein said filter means is situated in said retaining part.

36. The device of claim 32 further comprising means for detachably mounting said cap means on said second engaging part.

37. The device of claim 33 wherein said member retaining part comprises a disc and wherein said disc is adapted to be received between said cap means and said second engaging part.

38. An ostomy device comprising a balloon-like member adapted to be inserted into the bowel and inflated to seal the stoma, said member comprising a flexible wall defining an opening, cap means for retaining said wall and closing said opening, means for adhering said cap means to the tissue proximate the stoma, said cap means comprising an inflation port and one-way valve means associated with said inflation port for preventing air from escaping through said inflation port.

39. The device of claim 38 further comprising means for inflating said member.

40. The device of claim 38 wherein said inflating means comprises a pressure relief valve.

41. The device of claim 38 wherein said cap means comprises flexible tube means connected to said port, said tube means being adapted to extend into said member and comprising an inflation channel.

42. The device of claim 41 wherein said inflating means comprises a hand pump comprising a nozzle adapted to be removably connected to said tube means, in communication with said inflation channel.

43. The device of claim 38 wherein said adhering means comprises a faceplate and means for detachably mounting said cap means on said faceplate.

44. The device of claim 43 wherein said faceplate comprises a first engaging part defining an opening, and said cap means mounting means comprises a second engaging part with an opening, said parts being adapted to engage, with said opening in said second engaging part aligned with the stoma.

45. The device of claim 38 wherein said member comprises a bulbous proximal end.

46. An ostomy device for insertion through the stoma into the bowel comprising a balloon-like member adapted to be inserted into the bowel and inflated to seal the stoma, said member comprising a flexible wall defining an opening, cap means for covering said opening, means for retaining said wall, said retaining means being adapted to be situated within said cap means, means for adhering said cap means to the tissue proximate the stoma, such that flatus from said bowel can pass between said member and the bowel wall, filter means situated in said retaining means for venting flatus and means for inflating member while cap means adheres to the tissue proximate the stoma.

47. The device of claim 46 further comprising means for inflating said member.

48. The device of claim 47 wherein said cap means comprises a port, flexible tube means connected to said port, said tube means being adapted to extend into said member and comprising an inflation channel.

49. The device of claim 48 wherein said inflating means further comprises pump means adapted to be connected to said inflation channel through said port.

50. The device of claim 47 herein said inflating means comprises a pressure relief valve.

51. The device of claim 48 wherein said tube means comprises a one-way valve.

52. The device of claim 46 wherein said adhering means comprises a faceplate and means for detachably mounting said cap means on said faceplate.

53. The device of claim 52 wherein said faceplate comprises a first engaging part defining an opening, and said cap means mounting means comprises a second engaging part with an opening, said parts adapted to engage, with said opening in said second engaging part aligned with the stoma.

54. The device of claim 53 wherein said member retaining means has an opening and further comprising a waste collection receptacle having a first inlet aligned with said second engaging part opening and a wall defining a second inlet, said receptacle wall being sealed to said member retaining means with said second inlet aligned with said opening in said member retaining means.

55. The device of claim 53 further comprising means for detachably mounting said cap means on said second engaging part.

56. The device of claim 46 wherein said member comprises a bulbous proximal end.

57. An ostomy device for insertion through the stoma into the bowel comprising a balloon-like member adapted to be inserted into the bowel and inflated to seal the stoma, said member comprising a flexible wall defining an opening, cap means for closing said opening, means for retaining said wall, means for adhering said cap means to the tissue proximate the stoma, means for collection of waste from the bowel upon removal of said cap means, said waste collection means being operably connected between said wall retaining means and said adhering means, externally to the stoma and means for inflating said member while said cap means adheres to the tissue proximate the stoma.

58. The device of claim 57 wherein said waste collection means is stored within said cap means.

59. The device of claim 57 further comprising means for inflating said member.

60. The device of claim 59 wherein said cap means comprises a port, flexible tube means connected to said port, said tube means being adapted to extend into said member and comprising an inflation channel.

61. The device of claim 60 wherein said inflating means further comprises pump means adapted to be connected to said inflation channel through said port.

62. The device of claim 60 wherein said tube means comprises a one-way valve.

63. The device of claim 60 wherein said inflating means comprises a hand pump comprising a nozzle adapted to be removably connected to said tube means, in communication with said inflation channel.

64. The device of claim 59 wherein said inflating means comprises a pressure relief valve.

65. The device of claim 57 wherein said adhering means comprises a faceplate and means for detachably mounting said cap means on said faceplate.

66. The device of claim 65 wherein said faceplate comprises a first engaging part defining an opening, and said cap means mounting means comprises a second engaging part with an opening, said parts being adapted to engage, with said opening in said second engaging part aligned with the stoma.

67. The device of claim 66 wherein said cap means mounting means further comprises a member retaining part defining an opening, said waste collection receptacle having a first inlet aligned with said second engaging part opening and a wall defining a second inlet, said receptacle wall being sealed to said member retaining part with said second inlet aligned with said opening in said member retaining part.

68. The device of claim 66 further comprising means for detachably mounting said cap means on said second engaging part.

69. The device of claim 67 wherein said member retaining part comprises a disc and wherein said disc is adapted to be received between said cap means and said second engaging part.

70. The device of claim 57 wherein said member comprises a bulbous proximal end.

71. An ostomy device for insertion through the stoma into the bowel comprising a balloon-like member adapted to be inserted into the bowel and inflated to seal the stoma, said member comprising a flexible wall defining an opening, cap means for retaining said wall and closing said opening and means for adhering said cap means to the tissue proximate the stoma, means for inflating said member, wherein said cap means comprises a port, flexible tube means connected to said port, said tube means being adapted to extend into said member and comprising an inflation channel, wherein said inflating means comprises a hand pump comprising a nozzle adapted to be removably connected to said tube means, in communication with said inflation channel, said adhering means comprising a faceplate, means for detachably mounting said cap means on said faceplate, said faceplate comprising a first engaging part defining an opening, a second engaging part with an opening, said parts being adapted to engage, with said opening in said second engaging part aligned with the stoma, wherein said detachable mounting means further comprises a member retaining part defining an opening and a waste collection receptacle having a first inlet aligned with said second engaging part opening and a wall defining a second inlet, said receptacle wall being sealed to said member retaining part with said second inlet aligned with said opening in said member retaining part.

72. An ostomy device for insertion through the stoma into the bowel comprising a balloon-like member adapted to be inserted into the bowel and inflated to seal the stoma, said member comprising a flexible wall defining an opening, cap means for retaining said wall and closing said opening, and means for adhering said cap means to the tissue proximate the stoma, wherein said adhering means comprises a faceplate, means for detachably mounting said cap means on said faceplate, means for inflating said member, said cap means comprising a port, flexible tube means connected to said port, said tube means being adapted to extend into said member and comprising an inflation channel, wherein said inflating means comprises a hand pump comprising a nozzle adapted to be removably connected to said tube means, in communication with said inflation channel.

73. An ostomy device for insertion through the stoma into the bowel comprising a balloon-like member adapted to be received in the bowel and inflated to seal the stoma, a faceplate, means for adhering said faceplate to the tissue surrounding the stoma, said member comprising a flexible wall defining an opening, cap means for retaining said wall and closing said opening in said member, said cap means comprising an inflation port, and means for mounting said cap means on said faceplate, and a waste collection receptacle operably interposed between said cap means and said faceplate, wherein said cap means mounting means comprises means for detachably engaging said faceplate and means for detachably mounting said cap means on said faceplate engaging means, further comprising a channel defined between said wall of said member and the interior wall of said receptacle, and filter means operably interposed between said channel and the environment.

74. The device of claim 73 wherein said cap means mounting means comprises a member retaining part to which said member wall is affixed.

75. The device of claim 73 wherein said cap means mounting means comprises a member retaining part to which said member wall is affixed, said filter means being situated in said retaining part.

76. An ostomy device for insertion through the stoma into the bowel comprising a balloon-like member adapted to be inserted into the bowel and inflated to seal the stoma, said member comprising a flexible wall defining an opening, cap means for retaining said wall and closing said opening and means for adhering said cap means to the tissue proximate the stoma, wherein said adhering means comprises a faceplate, means for detachably mounting said cap means on said faceplate, said faceplate comprising a first engaging part defining an opening, and said cap means mounting means comprising a second engaging part with an opening, said parts being adapted to engage with said opening in said second engaging part aligned with the stoma, said cap means mounting means further comprising a member retaining part defining an opening and a waste collection receptacle having a first inlet aligned with said second engaging part opening and a wall defining a second inlet, said receptacle wall being sealed to said member retaining part with said second inlet aligned with said opening in said member retaining part.

77. An ostomy device for insertion through the stoma into the bowel comprising a balloon-like member adapted to be inserted into the bowel and inflated to seal the stoma, said member comprising a flexible wall defining an opening, cap means for retaining said wall and closing said opening, means for adhering said cap means to the tissue proximate the stoma, said cap means comprising an inflation port and one-way valve means associated with said inflation port for preventing air from escaping through said inflation port, said adhering means comprising a faceplate, means for detachably mounting said cap means on said faceplate, said faceplate comprising a first engaging part defining an opening, and said cap means mounting means comprises a second engaging part with an opening, said parts being adapted to engage, with said opening in said second engaging part aligned with the stoma, said cap means mounting means further comprising a member retaining part defining an opening and a waste collection receptacle having a first inlet aligned with said second engaging part opening and a wall defining a second inlet, said receptacle wall being sealed to said member retaining part.

78. An ostomy device for insertion through the stoma into the bowel comprising a balloon-like member adapted to be inserted into the bowel and inflated to seal the stoma, said member comprising a flexible wall defining an opening, cap means for retaining said wall and closing said opening, means for adhering said cap means to the tissue proximate the stoma, said cap means comprising an inflation port and one-way valve means associated with said inflation port for preventing air from escaping through said inflation port, said cap means comprising flexible tube means connected to said port, said tube means being adapted to extend into said member and comprising an inflation channel, and inflating means comprising a hand pump comprising a nozzle adapted to be removably connected to said tube means, in communication with said inflation channel.

79. The device of claim 78, wherein said inflating means further comprises pump means adapted to be connected to said inflation channel through said port.

80. The device of claim 78 wherein said cap means mounting means further comprises a member retaining part defining an opening and a waste collection receptacle having a first inlet aligned with said second engaging part opening and a wall defining a second inlet, said receptacle wall being sealed to said member retaining part.

81. The device of claim 80 further comprising a channel defined between said wall of said member and the interior wall of said receptacle and filter means operably interposed between said channel and the environment.

82. The device of claim 81 wherein said filter means is situated in said retaining part.

83. The device of claim 80 wherein said member retaining part comprises a disc and wherein said disc is adapted to be received between said cap means and said second engaging part.

84. The device of claim 78 further comprising means for detachably mounting said cap means on said second engaging part.

85. An ostomy device for insertion through the stoma into the bowel comprising a balloon-like member adapted to be inserted into the bowel and inflated to seal the stoma, said member comprising a flexible wall defining an opening, cap means for retaining said wall and closing said opening, means for adhering said cap means to the tissue proximate the stoma, means for inflating said member and pressure relief valve means associated with said inflation means to prevent overinflation of said member, said adhering means comprising a faceplate, means for detachably mounting said cap means on said faceplate, said faceplate comprising a first engaging part defining an opening, said cap means mounting means comprising a second engaging part with an opening, said parts being adapted to engage, with said opening in said second engaging part aligned with the stoma, said cap means mounting means further comprises a member retaining part defining an opening and a waste collection receptacle having a first inlet aligned with said second engaging part opening and a wall defining a second inlet, said receptacle wall being sealed to said member retaining part with said second inlet aligned with said opening in said member retaining part.

86. The device of claim 85 further comprising a channel defined between said wall of said member and the interior wall of said receptacle and filter means operably interposed between said channel and the environment.

87. The device of claim 86 wherein said filter means is situated in said retaining part.

88. The device of claim 85 wherein said member retaining part comprises a disc and wherein said disc is adapted to be received between said cap means and said second engaging part.

89. An ostomy device for insertion through the stoma into the bowel comprising a balloon-like member adapted to be inserted into the bowel and inflated to seal the stoma, said member comprising a flexible wall defining an opening, cap means for retaining said wall and closing said opening, means for adhering said cap means to the tissue proximate the stoma, means for inflating said member, pressure relief valve means associated with said inflation means to prevent over inflation of said member, said inflating means comprising a hand pump comprising a nozzle adapted to be removably connected to said tube means, in communication with said inflation channel.

90. The device of claim 89 wherein said cap means comprises a port, flexible tube means connected to said port, said tube means being adapted to extend into said member and comprising an inflation channel.

91. The device of claim 90 wherein said inflating means further comprises pump means adapted to be connected to said inflation channel through said port.

92. The device of claim 90 wherein said tube means comprises a one-way valve.

93. The device of claim 89 wherein said adhering means comprises a faceplate and means for detachably mounting said cap means on said faceplate.

94. The device of claim 93 wherein said faceplate comprises a first engaging part defining an opening, and said cap means mounting means comprises a second engaging part with an opening, said parts being adapted to engage, with said opening in said second engaging part aligned with the stoma.

95. The device of claim 94 wherein said cap means mounting means further comprises a member retaining part defining an opening and a waste collection receptacle having a first inlet aligned with said second engaging part opening and a wall defining a second inlet, said receptacle wall being sealed to said member retaining part with said second inlet aligned with said opening in said member retaining part.

96. The device of claim 94 further comprising means for detachably mounting said cap means on said second engaging part.

97. The device of claim 89 wherein said inflating means comprises a hand pump comprising a nozzle adapted to be removably connected to said tube means, in communication with said inflation channel.

98. The device of claim 89 wherein said member comprises a bulbous proximal end.

99. An ostomy device for insertion through the stoma into the bowel comprising a balloon-like member adapted to be inserted into the bowel and inflated to seal the stoma, said member comprising a flexible wall defining an opening, cap means for covering said opening, means for retaining said wall, said retaining means being adapted to be situated within said cap means, means for adhering said cap means to the tissue proximate the stoma, such that flatus from said bowel can pass between said member and the bowel wall, and filter means situated in said retaining means for venting flatus, said adhering means comprising a faceplate, means for detachably mounting said cap means on said faceplate, said faceplate comprising a first engaging part defining an opening, and said cap means mounting means comprises a second engaging part with an opening, said parts adapted to engage, with said opening in said second engaging part aligned with the stoma, said member retaining means having an opening and further comprising a waste collection receptacle having a first inlet aligned with said second engaging part opening and a wall defining a second inlet, said receptacle wall being sealed to said member retaining means with said second inlet aligned with said opening in said member retaining means.

100. The device of claim 99 wherein said member retaining means comprises a disc and wherein said disc is adapted to be received between said cap means and said second engaging part.

101. The device of claim 48 wherein said inflating means comprises a hand pump comprising a nozzle adapted to be removably connected to said tube means, in communication with said inflation channel.

102. An ostomy device for inserting through the stoma into the bowel comprising a balloon-like member adapted to be inserted into the bowel and inflated to seal the stoma, said member comprising a flexible wall defining an opening, cap means for covering said opening, means for retaining said wall, said retaining means being adapted to be situated within said cap means, means for adhering said cap means to the tissue proximate the stoma, such that flatus from said bowel can pass between said member and the bowel wall, and filter means situated in said retaining means for venting flatus, said adhering means comprising a faceplate, means for detachably mounting said cap means on said faceplate, said faceplate comprising a first engaging part defining an opening, and said cap means mounting means comprises a second engaging part with an opening, said parts adapted to engage, with said opening in said second engaging part aligned with the stoma, further comprising means for detachably mounting said cap means on said second engaging part.

103. An ostomy device for insertion through the stoma into the bowel comprising a balloon-like member adapted to be inserted into the bowel and inflated to seal the stoma, said member comprising a flexible wall defining an opening, cap means for closing said opening, means for retaining said wall, means for adhering said cap means to the tissue proximate the stoma and means for collection of waste from the bowel upon removal of said cap means, said waste collection means being operably connected between said wall retaining means and said adhering means, externally to the stoma, said adhering means comprising a faceplate and means for detachably mounting said cap means on said faceplate, said faceplate comprising a first engaging part defining an opening, and said cap means mounting means comprises a second engaging part with an opening, said parts being adapted to engage, with said opening in said second engaging part aligned with the stoma, wherein said cap means mounting means further comprises a member retaining part defining an opening, said waste collection receptacle having a first inlet aligned with said second engaging part opening and a wall defining a second inlet, said receptacle wall being sealed to said member retaining part with said second inlet aligned with said opening in said member retaining part.

104. The device of claim 103 further comprising a channel defined between said wall of said member and the interior wall of said receptacle and filter means operably interposed between said channel and the environment.

105. The device of claim 104 wherein said filter means is situated in said retaining part.

106. An ostomy device for insertion through the stoma into the bowel comprising a balloon-like member adapted to be inserted into the bowel and inflated to seal the stoma, said member comprising a flexible wall defining an opening, cap means for closing said opening, means for retaining said wall, means for adhering said cap means to the tissue proximate the stoma and means for collection of waste from the bowel upon removal of said cap means, said waste collection means being operably connected between said wall retaining means and said adhering means, externally to the stoma, said adhering means comprising a faceplate and means for detachably mounting said cap means on said faceplate, wherein said faceplate comprises a first engaging part defining an opening, and said cap means mounting means comprises a second engaging part with an opening, said parts being adapted to engage, with said opening in said second engaging part aligned with the stoma, further comprising means for detachably mounting said cap means on said second engaging part.

107. An ostomy device for insertion through the stoma into the bowel comprising a balloon-like member adapted to be inserted into the bowel and inflated to seal the stoma, said member comprising a flexible wall defining an opening, cap means for closing said opening, means for retaining said wall, means for adhering said cap means to the tissue proximate the stoma and means for collection of waste from the bowel upon removal of said cap means, said waste collection means being operably connected between said wall retaining means and said adhering means, externally to the stoma, said cap means comprising a port, flexible tube means connected to said port, said tube means being adapted to extend into said member and comprising an inflation channel, said inflating means comprising a hand pump comprising a nozzle adapted to be removably connected to said tube means, in communication with said inflation channel.

108. An ostomy device for insertion through the stoma into the bowel comprising a balloon-like member adapted to be received in the bowel and inflated to seal the stoma, a faceplate, means for adhering said faceplate to the tissue surrounding the stoma, said member comprising a flexible wall defining an opening, cap means for retaining said wall and closing said opening in said member, means for mounting said cap means on said faceplate and means for inflating said member while said cap means is mounted on said faceplate.

109. The device of claim 108 further comprising a waste collection receptacle operably interposed between said cap means and said faceplate.

110. The device of claim 77 wherein said cap means mounting means comprises means for detachably engaging said faceplate and means for detachably mounting said cap means on said faceplate engaging means.

111. The device of claim 108 wherein said faceplate comprises a first engaging part and cap means mounting means comprises a second engaging part.

112. The device of claim 108 wherein said cap means comprises flexible tube means comprising an inflation channel connected to said inflation port.

113. The device of claim 112 further comprising a one-way valve associated with said inflation channel.

114. The device of claim 108 wherein said inflating means comprises a hand pump comprising a nozzle adapted to be removably connected to said inflation port.

* * * * *